United States Patent [19]

Singh

[11] Patent Number: 4,505,735

[45] Date of Patent: Mar. 19, 1985

[54] TETRA-N-SUBSTITUTED UREA DERIVATIVES AS HERBICIDES

[75] Inventor: Rajendra K. Singh, Maryland Hts., Mo.

[73] Assignee: Monsanto Co., St. Louis, Mo.

[21] Appl. No.: 459,447

[22] Filed: Jan. 20, 1983

[51] Int. Cl.[3] ..................... A01N 57/22; A01N 57/24; C07F 9/40; C07F 9/65

[52] U.S. Cl. ..................................... 71/086; 260/938; 544/157

[58] Field of Search ........................ 260/938; 544/157; 71/86

[56] References Cited

U.S. PATENT DOCUMENTS

| | | | |
|---|---|---|---|
| 4,191,552 | 3/1980 | Large et al. | 71/86 |
| 4,328,027 | 5/1982 | Buren et al. | 71/86 |

*Primary Examiner*—Anton H. Sutto

*Attorney, Agent, or Firm*—David Bennett; Richard H. Shear; Arnold H. Cole

[57] ABSTRACT

It is found that certain novel tetra-substituted urea derivatives have herbicidal properties. The derivatives bear, on the same nitrogen atom a cyanomethyl group and an esterified methylene phosphonic acid group.

4 Claims, No Drawings

TETRA-N-SUBSTITUTED UREA DERIVATIVES AS HERBICIDES

BACKGROUND OF THE INVENTION

This invention relates to novel tetra N-substituted derivatives of urea that have been shown to possess herbicidal activity.

The compounds of the invention bear on one nitrogen atom, one methylenephosphonate group and thus can be regarded as members of the glyphosate (N-phosphonomethylglycine) family of herbicidal compounds.

DESCRIPTION OF THE INVENTION

The compounds of the invention have the formula

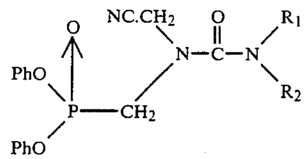

wherein Ph indicates a phenyl group and $R_1$ and $R_2$ are each individually, methyl or ethyl or, taken together, a morpholino group.

The compounds in which $R_1$ and $R_2$ are each methyl are found to display significantly higher activity than related compounds and are therefore particularly preferred over the alternatives.

The compounds of the invention are produced by the following reaction:

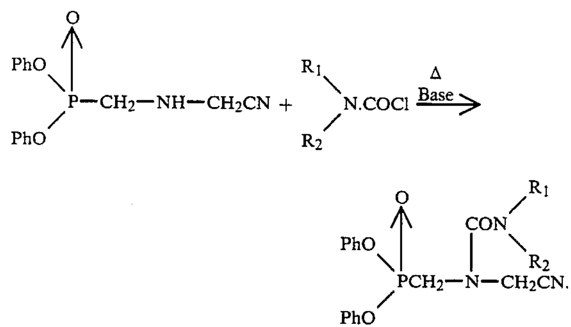

where Ph, $R_1$ and $R_2$ have the meanings indicated above.

The starting nitrile derivative,

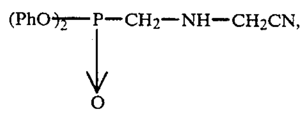

is described in U.S. Pat. No. 4,067,719 and can readily be obtained using the techniques described in that patent.

The process of the invention is conducted in the presence of a strong organic base. This can be a base such as triethylamine but it is found that generally higher conversions are obtained using the somewhat stronger base, diazabicycloundecene (DBU).

In order to enhance the reaction rate, it is preferred to heat the reactants preferably in such a wat that the reaction is conducted at reflux temperatures. Even so, several hours are usually required to reach a satisfactory level of conversion to the desired end product.

The reaction medium is preferably an organic solvent such as toluene or tetrahydrofuran though this is not a critical feature of the invention.

DESCRIPTION OF THE PREFERRED EMBODIMENTS

The invention is now further described with reference to the following examples which are for the purpose of illustration only and are intended to imply no limitation on the essential scope of the invention.

EXAMPLE 1

This example describes the production of the diphenyl ester of N(dimethylcarbamoyl)-N-(cyanomethyl)aminomethyl phosphonic acid which has the formula

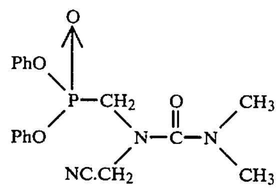

A reaction mixture of 6.04 gm of the diphenyl ester of N-(cyanomethyl)aminomethyl phosphonic acid, 4.30 gm of N,N dimethylcarbamoyl chloride and 5.05 gm of triethylamine were dissolved in 50 ml of toluene. This mixture was heated under reflux for approximately three days under a nitrogen atmosphere before being diluted with 150 ml of ether and then filtered. The filtrate was then concentrated and left under a low vacuum overnight.

The product was separated from the reaction mixture chromatographically using a column of 100 gm of silica gel and an elutant of cyclohexane and ethyl acetate in 1:1 volume ration. A total of 4.35 gm of product was separated.

The empirical formula of the compound to be produced is $C_{18}H_{20}N_3O_4P_1$ and this predicts elemental proportions of C—57.91%; H—5.40%; and 11.20%. Elemental analysis of the product showed: 57.79% of C; 5.44% of hydrogen; and 11.17% of nitrogen.

EXAMPLE 2

This example describes the production of the diphenyl ester of [N-(cyanomethyl),N-(diethylcarbamoyl)]amino methyl phosphonic acid:

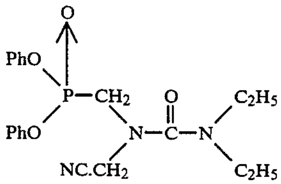

A reaction mixture of 6.04 gm of the diphenyl ester of N-(cyanomethyl)amino methyl phosphonic acid, 3.387 gm of N,N-diethyl carbamoyl chloride, 3.38 gm of diazabicycloundecene in 50 ml of tetrahydrofuran was refluxed under nitrogen for four days. The solvent was then largely removed and 150 ml of chloroform were added and this diluted mixture was then washed twice with water and dried over magnesium sulfate. After filtration through celite (clay) and removal of the solvent, 634 gm of crude product were obtained.

This was then chromatographed over 150 gm of silica gel using a 60:40(v/v) cyclohexane/ethyl acetate elutant and then re-chromatographed using 100 gm of silica gel and a 70:30 (v/v) cyclohexane/ethyl acetate elutant to yield 1.2 gm of purified product.

The empirical formula of the above compound is $C_{20}H_{24}N_3O_4P_1$ so that the expected elemental proportions include C—59.84%, H—6.03% and N—10.47%. Elemental analysis of the product showed C—59.60% H—6.11% and N—10.32%.

EXAMPLE 3

This example describes the production of the diphenyl ester of N-(morpholinocarbamoyl)-N-(cyanomethyl) amino methyl phosphonic acid.

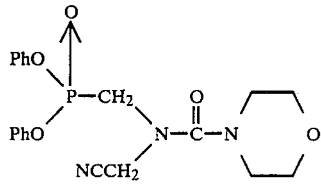

A reaction mixture comprising 6.04 gm of the diphenyl ester of N-(cyanomethyl)amino methyl phosphonic acid 4.5 gm of morpholinocarbamoyl chloride, 4.712 gm of diazobicycloundecene in 50 ml of tetrahydrofuran was refluxed under nitrogen for 14 hours.

The solvent was then largely removed and the remainder was taken up in 150 ml of chloroform. The solution was then thrice washed with water and brine after which it was dried over magnesium sulfate. Removal of solvent yielded 7.92 gm. of product.

The product was chromatographed over 180 gm of silica gel and eluted using a 60:40 (v/v) mixture of cyclohexane and ethyl acetate and then with ethyl acetate yielding 2.28 gm of a compound that solidified on standing and had a melting point of 97°-98° C.

The above compound has an empirical formula of C—57.83%, H—5.34%, N—10.12%, O—19.26% and P—7.46%. Elemental analysis of the product revealed C—57.78%, H—5.37% and N—10.12%

EXAMPLE 4

The post-emergent herbicidal activity of compounds of Examples 1-3 is demonstrated as follows. The active ingredient is applied in spray form to 14-21 day-old specimens of various plant species. The spray, a water or organic solvent-water solution containing active ingredient and a surfactant (35 parts butylamine salt of dodecylbenzenesulfonic acid and 65 parts tall oil condensed with ethylene oxide in the ratio of 11 moles ethylene oxide to 1 mole tall oil), is applied to the plants in different sets of pans at several rates (kg per hectare) of active ingredient. The treated plants are placed in a greenhouse and the effects are observed and recorded after approximately 4 weeks. The data is given in Table I.

The post-emergent herbicidal activity index used in Table I is as follows:

| Plant Response | Index |
|---|---|
| 0-24% Inhibition | 0 |
| 25-49% Inhibition | 1 |
| 50-74% Inhibition | 2 |
| 75-99% Inhibition | 3 |
| 100% Inhibition | 4 |

In the Table, the compounds are designated by the Example numbers and the plant species treated are each represented by a code letter as follows:

A. Cocklebur
B. Velvetleaf
C. Morningglory
D. Common Lambsquarters
E. Pennsylvania Smartweed
F. Yellow Nutsedge*
G. Quackgrass*
H. Johnsongrass*
I. Downy Brome
J. Barnyardgrass

*Established from vegetative propagules.

TABLE I

| Example | Applic. Level (Kg/Hect.) | A | B | C | D | E | F | G | H | I | J |
|---|---|---|---|---|---|---|---|---|---|---|---|
| 1 | 56 | 4 | 4 | 3 | 4 | 4 | 3 | 4 | 4 | 4 | 4 |
| 1 | 11.2 | 2 | 1 | 1 | 1 | 0 | 1 | 1 | 1 | | |
| 2 | 56 | 1 | 0 | 1 | 0 | 0 | 0 | 0 | 1 | 0 | 0 |
| 3 | 56 | 0 | 1 | 0 | 1 | 0 | 0 | 0 | 0 | 0 | 0 |

The herbicidal compositions, including concentrates which require dilution prior to application to the plants of this invention contain from 5 to 95 parts by weight of at least one active ingredient and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, all parts being by weight of the total composition. Where required from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carries and conditioning agents to provide compositions in the form of finely-divided particulate solids, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amines, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, polymethylene bisnapthalenesulfonate and sodium N-methyl-(long-chain acyl)taurates.

Water dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible powders of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Although compositions of this invention can also contain other additaments, for example, fertilizers, phytotoxicant and plant growth regulants, pesticides and the like used as adjuvants or in combination with any of the above-described adjuvants, it is preferred to employ the compositions of this invention alone with sequential treatments with the other phytotoxicants, fertilizers and the like for maximum effect. For example, the field could be sprayed with a composition of this invention either before or after being treated with fertilizers, other phytotoxicants and the like. The compositions of this invention can also be admixed with the other materials, e.g., fertilizers, other phytotoxicants, etc., and applied in a single application. Chemicals useful in combination with the active ingredients of this invention either simultaneously or sequentially include for example, triazines, ureas, carbamates, acetamides, acetanilides, uracils, acetic acids, phenols, thiolcarbamates, triazoles, benzoic acids, nitriles and the like.

Fertilizers useful in combination with the active ingredients include, for example, ammonium nitrate, urea, potash, and superphosphate.

When operating in accordance with the present invention effective amounts of the active ingredient are applied to above-ground portions of plants. The application of liquid and particulate solid herbicidal compositions to above-ground portions of plants can be carried out by conventional methods, e.g., powder dusters, boom recirculating and hand sprayers, rope wick applicators and spray dusters. The compositions can also be applied from airplanes as a dust or spray because of their effectiveness at low dosages. The application of herbicidal compositions to aquatic plants is usually carried out by spraying the compositions on the aquatic plants in the area where inhibition of the aquatic plants is desired.

The application of an effective amount of the compounds of this invention to the plant is essential and critical for the practice of the present invention. The exact amount of active ingredient to be employed is dependent upon such factors as the plant species and stage of development thereof, and the amount of rainfall as well as the specific compound employed. In foliar treatment for the inhibition of vegetative growth, the active ingredients are applied in amounts from about 5 to about 75 or more kilograms per hectare. In applications for the inhibition of aquatic plants, the active ingredients are applied in amounts of from about 1.0 parts per million to about 1000 parts per million, based on the aquatic medium. An effective amount for phytotoxic or herbicidal action is that amount necessary for overall or selective control, i.e., a phytotoxic or herbicidal amount. It is believed that one skilled in the art can readily determine from the teachings of this specification, including examples, the approximate application rate.

Although the invention is described with respect to specific modifications, the details thereof are not to be construed as limitations except to the extent indicated in the following claims.

What is claimed is:

1. A compound having the formula:

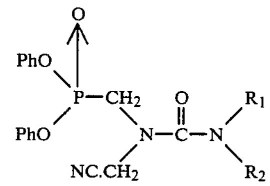

where each Ph is a phenyl group and $R_1$ and $R_2$ are each individually methyl or ethyl groups or, together with the nitrogen privide a morpholino radical.

2. A compound according to claim 1 in which both $R_1$ and $R_2$ are methyl groups.

3. A herbicidal composition comprising an adjuvant and a herbicidally effective amount of the compound of claim 2.

4. A herbicidal process which comprises applying to a plant a herbicidally effective amount of the compound of claim 2.

* * * * *